United States Patent [19]

Carter, II

[11] 4,390,632

[45] Jun. 28, 1983

[54] STABILIZATION PROCESS FOR BIOLOGICAL CELLS AND STABILIZED COMPOSITIONS THEREOF

[75] Inventor: James H. Carter, II, Ft. Lauderdale, Fla.

[73] Assignee: Coulter Electronics, Inc., Hialeah, Fla.

[21] Appl. No.: 167,803

[22] Filed: Jul. 14, 1980

[51] Int. Cl.³ .......................................... G01N 33/48
[52] U.S. Cl. .................................. 436/10; 436/11; 436/17; 435/183
[58] Field of Search ............ 252/408; 23/230 B, 928; 424/2

[56] References Cited

U.S. PATENT DOCUMENTS 3,322,634  5/1967  Fulthorpe .......................... 424/12
4,198,206  4/1980  Ryan .............................. 23/230 B
4,199,471  4/1980  Louderback ........................ 252/408

Primary Examiner—Brooks H. Hunt
Assistant Examiner—M. Moskowitz
Attorney, Agent, or Firm—Silverman, Cass & Singer

[57] ABSTRACT

Biological cell compositions are stabilized to preserve aldehyde functionality by formation of acetal, particularly cyclic acetal, primarily in order to prevent cell-to-cell crosslinking. The stabilized biological cells are particularly useful as human blood particle analogs in reference reagents employed in electronic hematology testing instrumentation.

A process for preparing the acetal-stabilized biological cells employs reaction of polyaldehyde-treated biological cells with alcohol, preferably including 1,2 dialcohol, under acidic conditions; thereafter, the resulting product solution is adjusted to basic condition, stabilizing the acetal formation on the biological cells.

19 Claims, No Drawings

STABILIZATION PROCESS FOR BIOLOGICAL CELLS AND STABILIZED COMPOSITIONS THEREOF

BACKGROUND OF THE INVENTION

This invention relates to stabilization of biological cells, such as blood particles, for use in reference reagents employed in blood particle counting and sizing instruments. More particularly, this invention relates to stabilization of biological cells which have been treated for fixation with a polyaldehyde.

In the development of improved electronic blood particle counting and sizing equipment, such as the Coulter ® type instruments, increased descrimination between particle types as determined by size distributions has required continuing improvement in reference solutions of known or well-established particle concentration and size distributions for use as controls to insure that the instruments are performing properly. While fresh human blood can be modified to prepare whole blood hematology reference controls, such suspensions have limited shelf life and begin to lose stability after approximately thirty days, even under chilled storage; such instability results in alteration of the mean cell volume (MCV) with consequent decrease in reliable particle discrimination.

In an attempt to stabilize a liquid blood control standard by actual freezing with diol or triol additives, U.S. Pat. No. 4,199,471 teaches a treatment in which red cells are successively treated with aldehyde, followed by slow admixture with diol or triol, and retention in a buffered solution. The emphasis of this patent upon admixture of the diol or triol, in contrast to reaction, is illustrated by the use of formaldehyde as the preferred aldehyde in the examples of the disclosed treatment.

In another method disclosed in U.S. Pat. No. 4,160,644, a platelet reference control is stabilized by addition of a minor amount of solid polyethylene glycol either to the platelet suspension or to the diluent for the platelet suspension, whereby time and agitation stabilization are both achieved; liquid polyethylene glycol, having lower molecular weight, was found to be ineffective.

The use of separate reference control reagents for different particle types has been more difficult than use of whole blood controls. For example, any system for platelet counting that distinguishes human platelets from other cells in the blood sample based on the characteristic size range and volume distribution of platelets requires that the control material used must also closely simulate the same platelet size range and volume distribution. Any reference control containing platelets or simulated platelets that have a narrow size distribution range would not be useful to determine whether the size distribution limits were correctly set. To this end, the reference control material must have a mean size that lies between the upper and lower size limits and should have a volume distribution histogram that closely approximates the log-normal distribution of fresh human platelets.

Many types of technology have been applied to this problem to produce a product having suitable size, shape, and volume and electrical resistivity, as well as temperature and time stability, uniform particle dispersion and microbiologic inhibition. The principal types of particles investigated previously have been synthetic particles, such as polystyrene latex, non-animal yeast and pollen cells, chemically-fixed human or other mammalian platelets and chemically-fixed animal cells of other types. Synthetic particles may be manufactured to very close mean volume and size distribution specifications, but smooth, stable and uniform suspensions are very difficult to prepare. In addition, the spherical shape of these particles presents a different electronic "shape" to a Coulter Counter ®, and these volumes must be "corrected" for the difference in shape by an arbitrary shape factor. Introduction of an undefined mathematical factor into the control process is undesirable. Pollens and yeasts share these same disadvantages and, in addition, suffer from lack of uniformity from batch to batch and from lack of availability. Human and other animal platelets are rather difficult and expensive to collect and prepare. The preservation processes now in commercial use cause significant shrinkage of platelets which upsets the normal volume population distribution; and the platelets are adversely affected on aging from deterioration, thus limiting the usefulness of a given lot of platelet control.

In a method disclosed in U.S. Pat. No. 3,553,310, biological cells, such as goat erythrocyes and microbial cells, are stabilized by chemical fixation in reaction with aldehydes, particularly glutaraldehyde, to form particles which are preserved and stabilized against lysis. Although aldehyde fixation is desirable in terms of particle stability, such fixation also causes cross-linking that may occur between particles which leads to undesirable aggluttination.

Typically, only one of the aldehyde groups of glutaraldehye (1,5-pentandialdehyde, OHCCH$_2$CH$_2$CH$_2$CHO) reacts with a biological cell, for example an erythrocyte (RBC) membrane protein molecule, leaving the other aldehyde group free to cross-link with other adjacent functional groups on the same cell or on other cells.

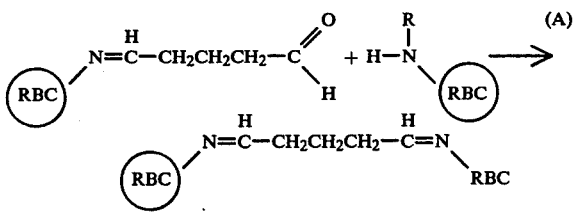

Other proposed mechanisms for this reaction involve formation of a glutaraldehyde dimer, containing a C=C with an active beta hydrogen. Condensation at this position leaves both aldehyde groups free.

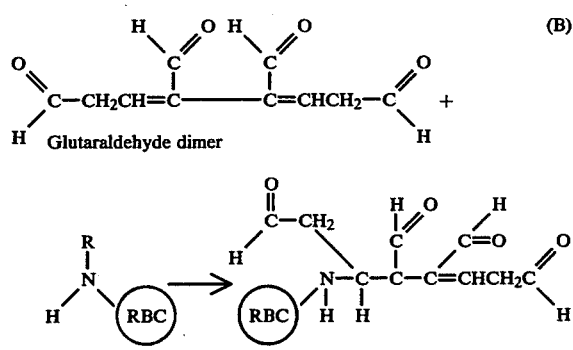

By either mechanism, pseudo-hemagglutination (i.e. cross-linking between adjacent cells) results, causing cell clumps that settle very rapidly and tend to stay matted on the container bottom. Although this process is a slow one, it seriously affects tha stability and usefulness of any analog control made in this manner.

SUMMARY OF THE INVENTION

In accordance with this invention, biological cells, which have been treated with polyaldehyde, can be stabilized to prevent cell-to-cell crosslinking of said cells by formation of acetal which preserves unreacted aldehyde functionality.

A process for preparing the acetal-stabilized biological cells comprises, reacting polyaldehyde-treated biological cells with an alcohol under acidic conditions; thereafter, the pH can be raised to basic condition, stabilizing the acetal formation.

In a preferred embodiment of this invention, the formation of cyclic acetal stabilizes the aldehyde-treated biological cells by employing a 1,3-dialcohol or 1,2-dialcohol, particularly ethylene glycol, to react with the free aldehyde.

The stabilized biological cells of this invention are particularly useful as human blood particle analogs in reference reagents employed in Coulter ®-type hematology testing instrumentation. Coulter ® and Coulter Counter ® are registered trademarks of Coulter Electronics, Inc. of Hialeah, Fla.

DETAILED DESCRIPTION OF THE INVENTION

Generally, biological cells, such as mammalian and avian erythroicytes employed as human blood particle analogs, have been fixed using aldehyde, particularly glutaraldehyde, as more fully described by Pearse in "Histochemistry: Theoretical and Applied", 3rd Ed., Vol. 1 (1968) at Chapter 5. While glutaraldehyde is the preferred aldehyde used for fixation of biological cells stabilized according to this invention, other polyaldehydes, such as, for example, oxalic, malonic, succinic and adipic dialdehydes, can be suitably employed for fixation of the biological cells.

Broadly, according to this invention, the unreacted or free aldehyde groups on the polyaldehyde-treated biological cells can be reacted with alcohol to form acetals, which prevent subsequent cell-to-cell crosslinking and stabilize the biological cells for use in suspensions having extended shelf-life without agglutination. Alcohols suitable for reaction with aldehydes to form acetals, for example, the alcohols having 1–6 carbon atoms, can be employed in this invention.

The preferred alcohols used in this invention react with the aldehyde to produce a cyclic acetal. Examples of such alcohols are the glycols which are not sterically hindered adjacent to the hydroxyl functions, such as trimethylene glycol (1,3-propane diol) which reacts with aldehyde to form a 6-membered cyclic acetal. Most preferred for use in this invention are the 1,2-dialcohols which react with aldehyde to form a 5-membered cyclic acetal resulting in particularly stabilized biological cells and promoting resistance to agglutination of the cells from suspension. Thus, propylene glycol and, particularly, ethylene glycol, are examples of the most preferred 1,2-dialcohols. Less preferable, glycerol is an example of a tri-hydric glycol which can form cyclic acetal but which leaves a free hydroxyl which can subsequently react to cross-link between biological cells with reduced resistance to agglutination. Other alcohols which can be employed according to this invention include 1,2-cyclopentanediol and 1,2-cyclohexanediol, for example.

To prepare the stabilized biological cells according to this invention, the polyaldehyde-treated cells are reacted with alcohol under acidic conditions to promote formation of the acetal; thus, the formation of the acetals is favored by reaction in the presence of excess alcohol to insure hydroxyl equivalent functionality greater than the reactive free aldehyde equivalent. For example, if 0.25% glutaraldehyde in saline is used to react in a suspension of approximately 75,000 to 100,000 cells per cubic millimeter, the reaction with ethylene glycol added to a concentration of about 3% (v/v) of the total suspension will provide suitable excess alcohol hydroxyl.

It has been determined that the reaction solution can be maintained at a pH preferably in the range of approximately 2.3–2.9 in order to promote the acetal formation on aldehyde-treated biological cells, such as animal erythrocytes, in solution containing excess hydroxyls. Subsequently, the resulting product solution can be adjusted to basic condition, preferably slightly over neutrality. It has been determined that adjustment of the resulting product solution to a pH preferably in the range approximately 7.2–7.6 is particularly effective in stabilizing the formed acetal stabilized biological cells. Suitable basic adjustment has been achieved by addition of a conventional phosphate buffer solution, and, if necessary, small amounts of a strong base, such as 6 N sodium hydroxide, can be added.

Representative of the stabilization reaction according to this invention is the following reaction in which gentaraldehyde-treated erythrocyte (RBC) reacts under acidic condition with ethylene glycol to form an ethyleneglycol cyclic acetal stabilization of the cell, which is particularly stable upon adjusting the product solution to basic condition:

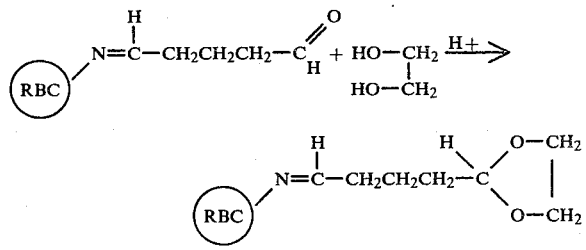

Stabilized biological cells prepared according to this invention have been developed for use as human blood particle analogs in reference solutions employed in hematology counting and sizing instruments. In such applications, the stabilized cells can be suspended in a diluent medium preferably containing suitable alcohol to prevent undesired transacetalization, and conventional bacteriocide and defoaming agents, with a buffer to maintain a pH of about 7.4. Best results have been obtained in producing human blood particle analogs by the preparation of animal erythrocytes, such as human and goat red blood cells, stabilized in accordance with this invention. For example, goat erythrocytes have been stabilized in accordance with this invention for use in blending a human platelet analog with a mean size in the range of 2-to 20 cubic microns and log-normal volume population. In similar application, human erythrocytes have been stabilized in accordance with this invention for use as human leukocyte or while blood cell (WBC) analogs. The stabilized cells can be used in stand-alone analogs or in whole blood simulations for control reference reagents.

The following example of the treatment of mammalian erythrocyte in accordance with the invention is illustrative:

EXAMPLE

Fresh goat blood was collected aseptically into anticoagulant. The blood was centrifuged slowly removing the plasma and anticoagulant. The erythrocytes were washed three times with phosphate buffered saline, pH 7.4 adjusted to approximately 410 milliosmoles per kilogram. Approximately 100 to 150 ml of the freshly washed erythrocytes were suspended in 2 L saline solution, 410 MOs/kg, and stirred with a magnetic stirrer. Next, 500 ml of a 0.31% (w/v) glutaraledehyde in 410 mOsm/kg saline solution were added dropwise at a flow rate of 10-15 ml per minute, followed by continued stirring for 15 minutes and further addition of 500 ml of a 0.44% (w/v)glutaraldehyde in 410 mOsm/kg saline at a flow rate of 10-15 ml per minute. After continued stirring for 15 minutes, 120 ml of ethylene glycol and 75 ml of 1 M glycine 0.5 M HCl buffer, pH 2.4, were added followed by stirring for 30 minutes. Final pH was 2.8±0.1. To the resulting solution, approximately 100 ml of 2 M phosphate buffer, pH 7.4 were added to bring pH to 7.4±0.2. The erythrocytes were settled overnight. After decanting the supernate, the erythrocytes were washed three times with water. The erythrocytes were then resuspended in a suspending medium to a count of 1 million±500,000/ml followed by placement in an ultrasonic bath for 1 to 2 hours to disintegrate clumps and filtration through a 20 micron microaggregate filter prior to final storage. The preparation was stable at room temperature.

| Formulation for Suspension Medium | | |
|---|---|---|
| 1L | | |
| Water | 800 ml | Q.S. to volume with |
| NaH$_2$PO$_4$ H$_2$O | 2.0 g | distilled water and filter |
| Na$_2$HPO$_4$ 7H$_2$O | 2.0 g | with a 0.2 micron filter. |
| Ethylene glycol | 150 ml | |
| 4-Chloro-3,5-xylenol, sodium | 0.5 g | |
| Na$_2$EDTA | 0.25 g | |
| Isopropanol | 100 ml | |

In applications such as the simulation of both lymphoid any myloid human leukocytes, stabilized cells from multiple species can be blended to obtain the desired dual volume cell population, typically requiring mean cell volume ranges of both 70-90 cubic microns and greater than 100 cubic microns for accurate human leukocyte analog in a whole blood control.

Those skilled in the art will readily appreciate the wide range of uses of the stabilized biological cells achieved by this invention. The examples delineated hereinabove are not intended to preclude a normal substitution of equivalent ingredients within the expected skill of the artisan in this field.

I claim:

1. A stabilized biological cell composition treated to comprise at least one acetal radical selected from the group consisting of

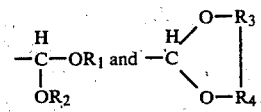

wherein $R_1$, $R_2$, $R_3$ and $R_4$ are groups having 1 to about 6 carbon atoms.

2. The composition as claimed in claim 1 wherein said acetal radical has said cyclic structure

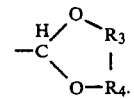

3. The composition as claimed in claim 2 wherein said cyclic structure includes

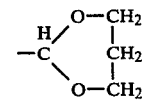

whereby $R_3$ is CH$_2$ and $R_4$ is CH$_2$CH$_2$.

4. The composition as claimed in claim 2 wherein said cyclic structure includes

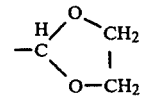

whereby $R_3$ is CH$_2$ and $R_4$ is CH$_2$.

5. The composition as claimed in claim 1, 2, 3, or 4 wherein said biological cell includes animal erythrocyte.

6. The composition as claimed in claim 5 wherein said animal erythrocyte includes at least one member selected from human erythrocytes and goat erythrocytes.

7. The composition as claimed in claim 6 further comprising, suspension diluent containing said stabilized cells.

8. A process for stabilizing the fixation of biological cells treated with a polyaldehyde, in order to prevent cell-to-cell cross-linking of said cells, comprising:
(a) reacting said aldehyde-treated biological cells with a least one alcohol in a solution maintained in acidic condition to form acetal, and thereafter,
(b) adjusting the resulting product solution from step (a) to basic condition.

9. The process as claimed in claim 8 wherein said acidic reaction solution in step (a) is maintained at a pH in the range of approximately 2.3 to 2.9.

10. The process as claimed in claim 8 wherein said acidic reaction solution in step (a) is maintained by addition of a solution of glycine and HCl.

11. The process as claimed in claim 8 wherein said alcohol includes at least one 1,2-diol.

12. The process as claimed in claim 11 wherein said 1,2-diol includes ethylene glycol.

13. The process as claimed in claim 8 wherein said basic condition is effected in step (b) by addition of phosphate buffer solution in an amount sufficient to achieve a pH in the range of approximately 7.2 to 7.6.

14. The process as claimed in claim 8, 9, 10, 11, 12, or 13 wherein said polyaldehyde includes glutaraldehyde.

15. The process as claimed in claim 8 wherein said biological cells include animal erythrocytes.

16. The process as claimed in claim 15, wherein said animal erythrocytes include goat erythrocytes for use as human platelet analog in reference solutions suitable for use in electronic hematology laboratory testing instrumentation.

17. The process as claimed in claim 15, wherein said animal erythrocytes include human erythrocytes for use as a human white blood cell analog in reference solutions suitable for use in electronic hematology labratory testing instrumentation.

18. A stabilized biological cell composition prepared by the process as claimed in claim 8.

19. A suspension of stabilized biological cells prepared by the process as claimed in claim 8.

* * * * *

UNITED STATES PATENT AND TRADEMARK OFFICE
CERTIFICATE OF CORRECTION

PATENT NO. : 4,390,632

DATED : June 28, 1983

INVENTOR(S) : JAMES HARRISON CARTER II

It is certified that error appears in the above-identified patent and that said Letters Patent are hereby corrected as shown below:

Column 5, line 44 change "2.0" to -- 0.2 --;

Column 5, line 52 change "any" to -- and --;

Column 6, line 49 change "a" to -- at --.

Signed and Sealed this

Eleventh Day of October 1983

[SEAL]

Attest:

GERALD J. MOSSINGHOFF

Attesting Officer    Commissioner of Patents and Trademarks